(12) United States Patent
El-Sherif et al.

(10) Patent No.: US 7,204,995 B2
(45) Date of Patent: Apr. 17, 2007

(54) TREATMENT AND CONTROL OF DRY EYE BY USE OF BIODEGRADABLE POLYMER CAPSULES

(76) Inventors: Dalia M. El-Sherif, 1117Hillcrest Rd., Penn Valley, PA (US) 19072; Jeylan A. El-Mansoury, 1117 Hillcrest Rd., Penn Valley, PA (US) 19072

( * ) Notice: Subject to any disclaimer, the term of this patent is extended or adjusted under 35 U.S.C. 154(b) by 556 days.

(21) Appl. No.: 10/355,772

(22) Filed: Jan. 31, 2003

(65) Prior Publication Data
US 2003/0143280 A1    Jul. 31, 2003

Related U.S. Application Data

(60) Provisional application No. 60/353,970, filed on Jan. 31, 2002.

(51) Int. Cl.
*A61F 2/00* (2006.01)
(52) U.S. Cl. ............ 424/427; 424/400; 424/422; 424/426; 128/260; 128/268
(58) Field of Classification Search ............ None
See application file for complete search history.

(56) References Cited

U.S. PATENT DOCUMENTS 3,867,519 A * 2/1975 Michaels ............ 424/473
3,981,303 A * 9/1976 Higuchi et al. ............ 424/428
3,986,510 A * 10/1976 Higuchi et al. ............ 424/428
3,993,071 A * 11/1976 Higuchi et al. ............ 424/428

OTHER PUBLICATIONS

Merck and Co. Disclosure, "Lacrisert" 1998.*

* cited by examiner

*Primary Examiner*—Michael P. Woodward
*Assistant Examiner*—Eric E. Silverman
(74) *Attorney, Agent, or Firm*—John S Munday

(57) ABSTRACT

A treatment for dry eye and other eye problems using a plug system or a delivery system. The plug system comprises solid, porous or hollow microcapsules composed of a biodegradable biocompatible polymer. The capsules are stored in the form of a powder that can be suspended in an aqueous carrier solution or dispersed in a gel or an ointment. Alternatively a biodegradable biocompatible capsule having a treating agent encapsulated within a polymer shell or a polymer sphere, again stored in the form of a powder that can be suspended in an aqueous carrier solution or dispersed in a gel or an ointment. The plug system prevents excretion of the capsules and their size is larger then the punctum and to prevent entrance to the lachrymal excretory system. The treatment is slowly released into the eye through the polymer shell or sphere and/or gets secreted as the polymer degrades.

17 Claims, 1 Drawing Sheet

A – Solid Capsule    B – Porous Capsule    C – Hollow Capsule

A    B

TREATMENT AND CONTROL OF DRY EYE BY USE OF BIODEGRADABLE POLYMER CAPSULES

This application claims priority from Provisional Application Ser. No. 60/353,970, filed Jan. 31, 2002.

FIELD OF THE INVENTION

The present invention relates to the treatment and control of dry eye problems. More particularly, the invention relates to the use of biodegradable polymer capsules for dry eye treatment and control.

BACKGROUND OF THE INVENTION

Many people suffer from what is called "Dry Eye". In which case the patient's eyes feel tired, scratchy or as though there were something grainy in them. The most common cause of dry eyes or tear dysfunction is due to aqueous deficiency and is best represented by Sjogrenis syndrome. Dry eyes tend to point to the insufficient production, distribution or retention of the tears. Naturally the tears need to be evenly retained and distributed across the corneal surface of the eye.

Natural tears are secreted by the lachrymal gland, which is located in the lateral orbit, and are evenly spread across the corneal surface of the eye and finally get excreted from the tear ducts (lachrymal puncti) to the nasolateral ducts which lead into the nose as illustrated in FIG. 1. The opening from the eye to the tear ducts is called the punctum, and the place which the tears get excreted from the eye. Movement of the eyelids helps distribute the tear across the eye.

The natural tear film consists of three layers, aqueous, mucin and lipid. The outer most layer is lipid, and comes from the meibomian gland. The middle aqueous layer is composed of water-soluble substances and comes mainly from the major and minor lachrymal glands, but also from accessory glands called glands of Krauss and Wolfring. The inner most layer is a mucinous layer is secreted by the globlet cells of the conjunctiva and from the lachrymal gland, this layer is composed of glycoproteins.

The mucin layer lies over the corneal and conjunctival epithelial cells.

The epithelial cell membrane is composed of lipoproteins and thus is hydrophobic. This hydrophobic environment is difficult to wet. Thus the presence of the mucin layer is to provide a hydrophilic surface for which the middle aqueous layer can now wet. The outer lipid layer is believed to prevent evaporation of the middle aqueous layer.

There are a variety of current treatments, and such treatment of dry eyes varies with the severity of the disease. For patients with slightly dry eyes, the use of drops in bottles should be sufficient, for those with moderate dry eyes the use of gels may be necessary, and finally for those experiencing severe dry eyes gels, ointments or minor surgery to occlude the tear duct may be needed.

Drops are simple salt solutions with additional ingredients that help them spread across the eye. The drops lubricate the eye making it feel better, but the effect is short lived and there is a need to reapply the drops often (about four times daily). This method of treatment is not very effective for overnight use and the patient tend to wake up with dry sore eyes. There are several different types of drops available on the market, examples of trade name products include, "Liquifilm", "Tears Natural", "Hypomellose", and "Snotears".

Tear drop preparations without preservatives (also called preservative free) do not contain preservatives and so can be used a lot more regularly then other types of drops without causing any type of toxicity or reaction secondary to the preservatives. "Minims" tears are drops contained within a small ampoule; this carries about 14 drops and may last a patient a full day with proper use. These are moderately expensive.

The use of gels to treat dry eyes is fairly new, the two types available under trade names are "Gel Tears" and "Viscotears". These last longer than drops and can be used for overnight treatment.

Ointments last even longer then gels. However, they may cause misty vision during the day if the treatment is applied at night. The two examples for this are "Simple" eye ointment and "lacrilube".

There is no cure for dry eyes yet and so the only treatment is to use one of the above-mentioned methods to lubricate, or keep the eye oily. These methods are not harmful to the eye, but are a hassle to the patient. The constant need to apply drops, gels or ointments is very inconvenient and for the elderly with shaky hands it is a challenge. These types of treatments are also very expensive.

While, drops, gels and ointments are available for the treatment of dry eye, the repetitive need for re-application makes them not only inconvenient to use but also an added challenge for many with unstable hands.

Accordingly it is an object of this invention to provide an improved dry eye treatment.

Another object is to provide a dry eye treatment that is relatively inexpensive.

Yet another object of this invention is to provide a dry eye treatment that is long lasting and easy to apply.

Other objects will appear hereinafter.

SUMMARY OF THE INVENTION

It has now been discovered that the above and other objects of the present invention may be accomplished in the following manner. Specifically, the present invention provides a technology that will reduce the re-application process of the dry eye treatment. This type of technology can be applied to various ophthalmic diseases such as glaucoma or postoperative conditions such as cataract surgery or refractive surgery.

The method of treatment for dry eyes employs a biodegradable biocompatible polymer capsule or capsules, that can be conveniently placed in the eye by the patient, to avoid drainage of the natural tear by blocking the lachrymal excretory system. The treatment for dry eyes employs a biodegradable biocompatible polymer capsule or capsules with an agent contained within them.

The polymer microcapsule may also include a treating agent whereby the polymer microcapsule is placed in the conjuntival sac of the patient's eye and releases the agent over a fixed period of time while the polymer microcapsule degrades.

Ophthalmic diseases that are treatable by the present invention, in addition to dry eye problems, include, glaucoma, post-operative conditions like cataract surgery or refractive surgery.

There are two parts to the present invention: a plug based system and a drug delivery based system. Both parts employ a biodegradable, biocompatible capsule.

BRIEF DESCRIPTION OF THE DRAWINGS

For a more complete understanding of the invention, reference is hereby made to the drawings, in which.

DETAILED DESCRIPTION OF THE PREFERRED EMBODIMENT

Figure 1:
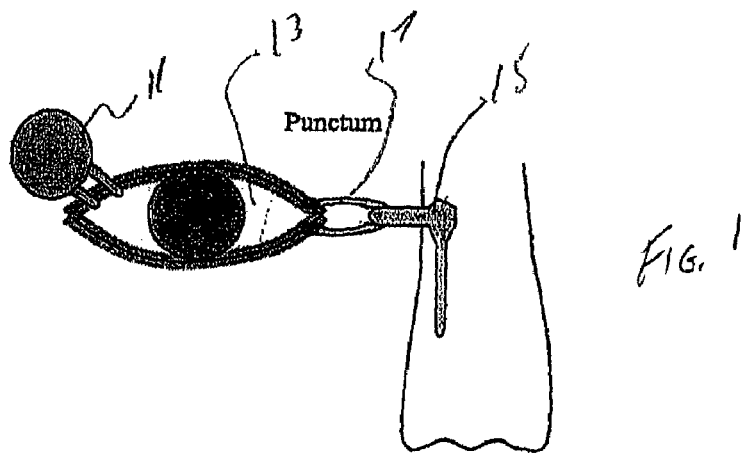
FIG. 1 is a schematic illustration of the secretion of tears flowing across the corneal surface of the eye.
Figure 2:
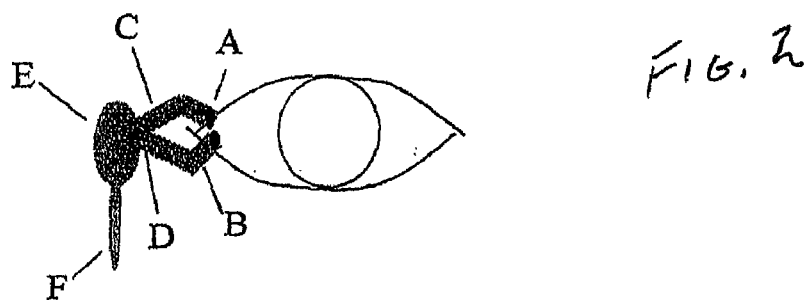
FIG. 2 is a schematic representation of the lachrymal excretory system of the eye.

As shown in FIG. 1, tears are secreted from the top left corner and the lachrymal gland 11, flow across the corneal surface of the eye 13 and the eyeball through the punctum 17 into the tear ducts 15 where they are excreted into the nose. In FIG. 2, the lachrymal excretory system is shown, where A is the punctum, B is the ampulla, C is the caniliculus, D is the common canaliculus, E is the lachrymal sac and F is the nasolacrimal duct.

As FIG. 2 depicts, the punctum (0.3–0.5 mm in diameter) is the entrance of the tear to the lachrymal excretory system. Once the tear has gone through the punctum it passes through the ampulla (2 mm in length) and then to the canaliculi (8 mm in length), where it then ends up in the common canaliculi prior to entering the lachrymal sac (10 mm) and finally existing through the nasolacrimal duct (12 mm in length).

Figure 3:
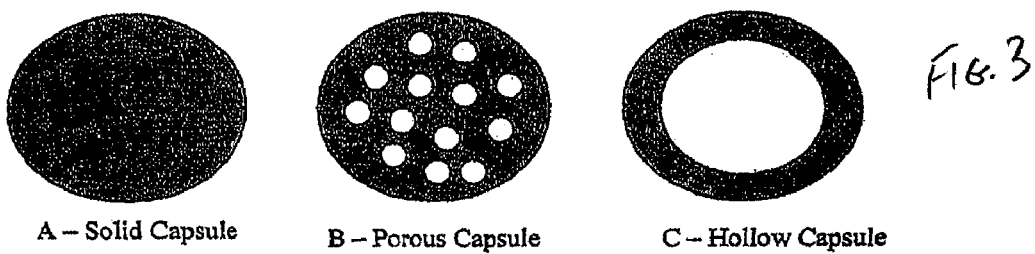
FIG. 3 is a schematic representation of three versions of the plug system of the present invention.

FIG. 3 illustrates three versions or embodiments of one embodiment or component of the present invention, showing the plug system. One embodiment comprises solid A, porous B, or hollow C, microcapsules that are in the size range of 0.01 mm to 1 mm. The capsules are composed of a biodegradable biocompatible polymer. The capsules are stored in the form of a powder that can be suspended in an aqueous carrier solution or dispersed in a gel or an ointment.

The purpose of these capsules is to plug the lachrymal excretory system. They may plug the system at the punctum, the ampulla, the canaliculi, lachrymal sac or nasolacrimal duct. There are three ways to place these plug systems. They can be dispersed in an aqueous carrier solution, and placed into the eye in the form of drops, or dispersed in a gel or ointment and placed in the eye in the form of a gel or ointment. The capsules will flow to the lachrymal excretory system with the carrier solution in the same manner the natural tear would flow. The size of the capsules would cause them get lodged in the lachrymal excretory system, the most likely place that this would occur is in the punctum, however depending on the size of the capsules, they may pass the punctum and accumulate elsewhere in the lachrymal excretory system, where the plug would occur.

Figure 4:
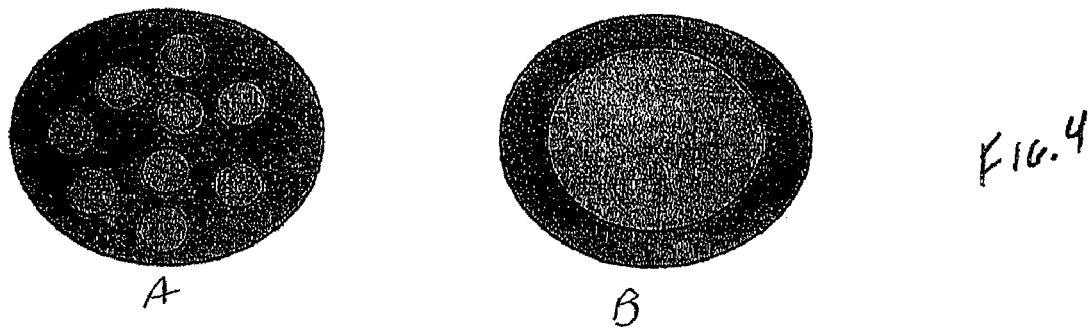
FIG. 4 is a schematic representation of the drug delivery system of the present invention, showing two embodiments thereof.

The drug delivery system shown in FIG. 4 is composed of a biodegradable biocompatible capsule (diameter of 0.01 mm to about 1 mm) associated with an agent. The drug delivery system capsule encapsulates an agent within a polymer shell A or within a polymer sphere B. The agent is anything used in the treatment of dry eyes can be a drop, gel or ointment. As with the plug system, the capsules are stored in the form of a powder that can be suspended in an aqueous carrier solution or dispersed in a gel or an ointment. The suspended capsules can be placed into the eye in the form of drops, and those dispersed in a gel or ointment can be placed in the eye in the form of a gel or ointment. The capsules will not get eliminated through the lachrymal excretory system for one of two reasons, they will be used with the plug system, which will prevent excretion of the capsules, or their size will be larger then the punctum and so their entrance to the lachrymal excretory system will be prevented. The drug delivery system works by slowly releasing the agent into the eye through the polymer shell or sphere and/or gets secreted as the polymer degrades. In this embodiment, the polymer microcapsule is placed in the conjuntival sac of the patient's eye and releases the agent over a fixed period of time while the polymer microcapsule degrades.

The life span of both the plug system and the drug delivery system will vary from hours to months depending on the material of which the capsule is composed and the different models used for each system. The plug system and the drug delivery systems can be used alone or in conjunction with each other depending on the medical situation. The number of capsules used for each situation is also dependent on the medical situation.

The capsule or capsules may come as a dry powder suspended in an aqueous solution or dispersed in a gel or ointment. The biodegradable biocompatible polymer capsule or capsules are placed into the patient's eye by the patient or by the physician in the form of drops, gels or ointments.

The capsules are made by a known double emulsion method. The polymer is dissolved in a solvent. Water or a treating agent is suspended in the polymer solution and probe sonicated, producing the first emulsion. The emulsion is then homogenized in a surfactant solution, producing the second emulsion. Stirring them in a solvent solution then dries the capsules. The capsules are collected and dried by centrifugation and freeze-drying respectively.

The size of the capsules and the encapsulation is dependent on variations of time, temperature, material used to fabricate the capsules. These factors also play a role as to which of the capsule models will be made.

In one embodiment where the treatment uses drops, the dry capsule or capsules may be reconstituted by a Pharmacist (prior to dispensing of the drops) or by the physician or patient in an aqueous solution prior to use and applied to the patient's eyes through a dropper.

The aqueous solution of the present invention include saline, carboxymethylcellulose sodium, Dextran, hydroxypropyl methycellulose, propylene and glycerin, as well as any ingredients of commercially available artificial tears.

When the invention is used with either gels or ointments, the dry capsule or capsules are readily dispersed in the ointment or gel prior to use by the physician or patient and may then be applied to the patient's eyes as a gel or ointment. One preferred gel is carboxymethylcellulose sodium salt as sell as any commercially available gel. Ointment includes petreolatum, mineral oil and any ingredients of commercially available ointments.

A preferred biodegradable biocompatible polymer capsule or capsules are solid, hollow or porous capsules with diameters in the range of 0.01 mm to 1 mm. The biodegradable biocompatible polymer capsule contains artificial tear drops, ophthalmic gels, or ophthalmic ointments and the like.

In a preferred embodiment, the diameter of the capsule or capsules is smaller or larger than the diameter of the punctum.

The polymer capsule or capsules of the present invention may be made of any biodegradable, biocompatible polymer.

Hydrogel based networks which may be biodegradable (enzymatic or hydrolytic) can be designed to increase in size in a controlled manner through swelling, which can improve the occlusion of the punctum. The material swells when exposed to an aqueous medium such as the fluids in the eye, and thus swell when in position. This material can be biodegradable or non biodegradable, since, over time, the biodegradable microcapsule will reduce in size, eventually exiting the punctum.

Preferred polymers are selected from the group consisting of a polylactide, polyglycolide, polycaprolactone, copolymers of polylactide and polyglycolide, copolymers of lactide and lactone, polysaccharides, polyanhydrides, polystyrenes, polyalkylcyanoacrylates, polyamides, polyphosphazenes, poly(methylmethacrylate), polyurethanes, copolymers of methacrylic acid and acrylic acid, copolymers of hydroxyethylmethacrylate and methylmethacrylate, polyaminoacids and polypeptides.

While particular embodiments of the present invention have been illustrated and described, it is not intended to limit the invention, except as defined by the following claims. It is contemplated that when the plug form is used, the plug may or may not be coated or otherwise containing a treating agent. Similarly, when the delivery system is used, it may be of a size to function as a plug or it may be smaller in size, thus requiring a second biodegradable, biocompatible polymer of the appropriate size to form a plug and retain the smaller biodegradable, biocompatible polymer containing a treating agent.

The invention claimed is:

1. A method for treating dry eye symptoms of a patient in the lachrymal excretory system of said patient, comprising the steps of:
   forming a biodegradable, biocompatible polymer into a microcapsule of from about 0.1 mm to about 1.0 mm and including a treating agent therein;
   placing said polymer microcapsule in a carrier solution to form a treating solution for placement of said polymer microcapsule in the eye of a patient; and
   positioning said polymer microcapsule to become lodged in the lachrymal excretory system of said patient for a period of time while said polymer microcapsule biodegrades.

2. The method of claim 1, wherein said polymer microcapsule is formed into a plug shape adapted to plug said extretory system at at least one location selected from the punctum, the ampulla, the canaliculi, the lachrymal sac and the nasolacrimal duct, said plug being formed into solid, porous or hollow polymer microcapsules.

3. The method of claim 1, wherein said agent is selected from the group consisting of saline, carboxymethylcellulose sodium, Dextran, hydroxypropyl methycellulose, propylene and glycerin.

4. The method of claim 1, wherein said polymer microcapsule is coated with a material adapted to swell in size when in contact with the fluids of the eye to prevent said microcapsule polymer from exiting the punctum until said polymer microcapsule has significantly biodegraded.

5. The method of claim 1, wherein said polymer is selected from the group consisting of polylactides, polyglycolides, polycaprolactones, copolymers of polylactides and polyglycolides, copolymers of lactide and lactone, polysaccharides, polyamides, polyanhydrides, polystyrenes, polyalkylcyanoacrylates, polyphosphazenes, poly(methylmethacrylate), polyurethanes, copolymers of methacrylic acid and acrylic acid, copolymers of hydroxyethylmethacrylate and methylmethacrylate, polyaminoacids and polypeptides.

6. A process for treating dry eye symptoms of a patient in the lachrymal excretory system of said patient, comprising:
   forming a biodegradable, biocompatible polymer into a microcapsule of from about 0.1 mm to about 1.0 mm and including a treating agent therein; and
   placing said polymer microcapsule in a carrier solution to form a treating solution;
   placing said treating solution in the eye of a patient; and
   positioning said polymer mirocapsule to become lodged in the lachrymal excretory system of said patient for a period of time while said polymer microcapsule biodegrades.

7. The process of claim 6, wherein said polymer microcapsule is formed into a plug shape adapted to plug said excretory system at at least one location selected from the punctum, the ampulla, the canaliculi, the lachrymal sac and the nasolacrimal duct.

8. The process of claim 7, wherein said plug comprises solid, porous or hollow polymer microcapsules.

9. The process of claim 6, wherein said agent is selected from the group consisting of saline, carboxymethylcellulose sodium, Dextran, hydroxypropyl methycellulose, and glycerin.

10. The process of claim 9, wherein said polymer microcapsule is coated with a material adapted to swell in size when in contact with the fluids of the eye to prevent said microcapsule polymer from exiting the punctum until said polymer microcapsule has significantly biodegraded.

11. The process of claim 6, wherein said polymer is selected from the group consisting of polylactides, polyglycolides, polycaprolactones, copolymers of polylactides and polyglycolides, copolymers of lactide and lactone, polysaccharides, polyamides, polyanhydrides, polystyrenes, polyalkylcyanoacrylates, polyphosphazenes, poly(methylmethacrylate), polyurethanes, copolymers of methacrylic acid and acrylic acid, copolymers of hydroxyethylmethacrylate and methylmethacrylate, polyaminoacids and polypeptides.

12. A process for treating dry eye symptoms of a patient in the lachrymal excretory system of said patient, comprising:
   forming a biodegradable, biocompatible polymer means for insertion into the eye of a patient into a microcapsule of from about 0.1 mm to about 1.0 mm and including a treating agent therein;
   placing said polymer microcapsule means in a carrier solution means for carrying said polymer microcapsule means to form a treating solution means for treating said eye symptoms;
   placing said treating solution means in the eye of a patient; and
   positioning said polymer microcapsule means to become lodged in the lachrymal excretory system of said patient for a period of time while said polymer microcapsule means biodegrades.

13. The process of claim 12, wherein said polymer means is formed into a plug shape adapted to plug said excretory system at at least one location selected from the punctum, the ampulla, the canaliculi, the lachrymal sac and the nasolacrimal duct.

14. The process of claim 13, wherein said plug comprises solid, porous or hollow microcapsule polymers.

15. The process of claim 12, wherein said agent is selected from the group consisting of saline, carboxymethylcellulose sodium, Dextran, hydroxypropyl methycellulose, propylene and glycerin, and ingredients of commercially available artificial tears.

16. The process of claim 15, wherein said polymer microcapsule means is coated with a material adapted to swell in size when in contact with the fluids of the eye to prevent said polymer microcapsule means from exiting the punctum until said microcapsule polymer has significantly biodegraded.

17. The process of claim 12, wherein said polymer is selected from the group consisting of polylactides, polyglycolides, polycaprolactones, copolymers of polylactides and polyglycolides, copolymers of lactide and lactone, polysaccharides, polyamides, polyanhydrides, polystyrenes, polyalkylcyanoacrylates, polyphosphazenes, poly(methylmethacrylate), polyurethanes, copolymers of methacrylic acid and acrylic acid, copolymers of hydroxyethylmethacrylate and methylmethacrylate, polyaminoacids and polypeptides.

* * * * *